United States Patent
Voronov et al.

(10) Patent No.: US 9,464,991 B2
(45) Date of Patent: Oct. 11, 2016

(54) METHOD FOR INSPECTING POLYSILICON LAYER

(71) Applicant: Samsung Display Co., Ltd., Yongin (KR)

(72) Inventors: Alexander Voronov, Yongin (RU); Suk-Ho Lee, Yongin (KR); Jae-Seung Yoo, Yongin (KR); Kyung-Hoe Heo, Yongin (KR); Gyoo-Wan Han, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 40 days.

(21) Appl. No.: 14/094,051

(22) Filed: Dec. 2, 2013

(65) Prior Publication Data

US 2014/0353523 A1    Dec. 4, 2014

(30) Foreign Application Priority Data

Jun. 4, 2013 (KR) .................. 10-2013-0064165

(51) Int. Cl.
*G01N 21/64* (2006.01)
*G01N 21/95* (2006.01)

(52) U.S. Cl.
CPC ...... *G01N 21/6489* (2013.01); *G01N 21/9501* (2013.01)

(58) Field of Classification Search
CPC .................................. G01N 21/6489
See application file for complete search history.

(56) References Cited

U.S. PATENT DOCUMENTS

| 5,406,214 | A | 4/1995 | Boda et al. |
|---|---|---|---|
| 5,612,539 | A | 3/1997 | Hoshi et al. |
| 7,113,276 | B1 | 9/2006 | Higgs et al. |
| 2004/0092042 | A1* | 5/2004 | Higgs .............................. 438/14 |
| 2007/0008518 | A1* | 1/2007 | Hummel et al. ........... 356/237.1 |
| 2008/0213926 | A1 | 9/2008 | Tajima et al. |
| 2008/0295882 | A1* | 12/2008 | Stephens et al. .............. 136/244 |
| 2009/0051914 | A1 | 2/2009 | Trupke et al. |
| 2009/0206287 | A1 | 8/2009 | Trupke et al. |
| 2010/0255588 | A1 | 10/2010 | Schenker |
| 2012/0057148 | A1* | 3/2012 | Voronov et al. ................ 356/51 |
| 2013/0062536 | A1* | 3/2013 | Bardos et al. ............. 250/459.1 |

FOREIGN PATENT DOCUMENTS

| JP | 2003-523628 | 8/2003 |
|---|---|---|
| KR | 10-1993-7003602 | 11/1993 |
| KR | 10-2003-0087677 | 11/2003 |

OTHER PUBLICATIONS

T. Trupke, et al., Progress with Luminescence Imaging for the Characterisation of Silicon Wafers and Solar Cells, 22nd European Photovoltaic Solar Energy Conference, Sep. 3-7, 2007, Milan, Italy, pp. 22-31.

Michio Tajima, et al., Mapping of Microdefects in Silicon Crystals by Photoluminescence at Room Temperature, Semiconductor Silicon 1990, Proceedings vol. 90-7, pp. 994-1004.

(Continued)

*Primary Examiner* — Casey Bryant
(74) *Attorney, Agent, or Firm* — H.C. Park & Associates, PLC

(57) ABSTRACT

A method for inspecting a polysilicon layer includes: radiating excitation light to the polysilicon layer; and detecting a photoluminescence signal generated by the excitation light, wherein average power of the excitation light has a range of 1 W/cm² to 10 W/cm², and peak power of the excitation light has a range of 100 W/cm² to 1000 W/cm².

10 Claims, 3 Drawing Sheets

(56) References Cited

OTHER PUBLICATIONS

T. Arguirov, et al., Photoluminescence study on defects in multicrystalline silicon, Phisica I tekhnica poluprovodnikov, 2007, vol. 41/4, pp. 450-453 (Russian journal).

R. Carius, et al., Band Tail States in Microcrystalline Silicon Solar Cells Probed by Photoluminescence and Open Circuit Voltage, Journal of Optoelectronics and Advanced Materials vol. 7, No. 1, Feb. 2005, pp. 121-128.

Mark J. Kerr, et al., General parameterization of Auger recombination in crystalline silicon, Journal of Applied Physics, vol. 91, N4, 2002, pp. 2473-2480, AIP Publishing LLC.

Karsten Bothe, "Oxygen-Related Trapping and Recombination Centers in Boron-doped Crystalline Silicon," PhD Dissertation, University of Hannover, Germany, ISBN 3-89959-474-6, Der Andere Verlag (2006): p. 98.

\* cited by examiner

METHOD FOR INSPECTING POLYSILICON LAYER

CROSS REFERENCE TO RELATED APPLICATION

This application claims priority from and the benefit of Korean Patent Application No. 10-2013-0064165, filed on Jun. 4, 2013, which is hereby incorporated by reference for all purposes as if fully set forth herein.

BACKGROUND

1. Field

The described technology relates generally to a method for inspecting a polysilicon layer. More particularly, the described technology relates generally to a method for inspecting the crystallinity and/or crystal structure of a polysilicon layer.

2. Discussion of the Background

Most flat panel display devices, such as an organic light emitting diode (OLED) display, a liquid crystal display (LCD), and the like, include a thin film transistor. Particularly, a low temperature polycrystalline silicon thin film transistor (LTPS TFT) having good carrier mobility can be applicable to a high speed operational circuit and can be used for a CMOS circuit, so the LPTS TFT has been commonly used.

A LTPS TFT includes a polysilicon film that is formed by crystallizing an amorphous silicon film. Methods for crystallizing the amorphous silicon film include solid phase crystallization, excimer laser beam crystallization, and metal catalyst crystallization.

Laser beam crystallization has been widely used because it is a relatively low temperature process that reduces the thermal deformation of a substrate and can be used to produce a polycrystalline silicon layer having excellent carrier mobility.

In order to determine whether a polysilicon layer is appropriately crystallized, light is radiated onto the polysilicon layer, and light discharged by the polysilicon layer is analyzed, in order to determine whether the polysilicon layer has a defect.

In order to properly determine the existence of the defect, the intensity of the excitation light radiated onto the polysilicon layer are conventionally be relatively high, and in this case, the thin-film polysilicon layer may be damaged.

The above information disclosed in this Background section is only for enhancement of the understanding of the background of the described technology, and therefore, it may contain information that does not constitute prior art.

SUMMARY

Exemplary embodiments of the present invention provide a high efficiency method for inspecting a polysilicon layer without damaging the thin-film polysilicon layer.

Additional features of the invention will be set forth in the description which follows, and in part will be apparent from the description, or may be learned by practice of the invention.

Exemplary embodiments of the present invention provide a method for inspecting a polysilicon layer that includes radiating excitation light onto the polysilicon layer, and detecting a photoluminescence signal generated by the excitation light.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention, illustrate exemplary embodiments of the invention, and together with the description serve to explain the principles of the invention.

DETAILED DESCRIPTION OF THE ILLUSTRATED EMBODIMENTS

Figure 1:
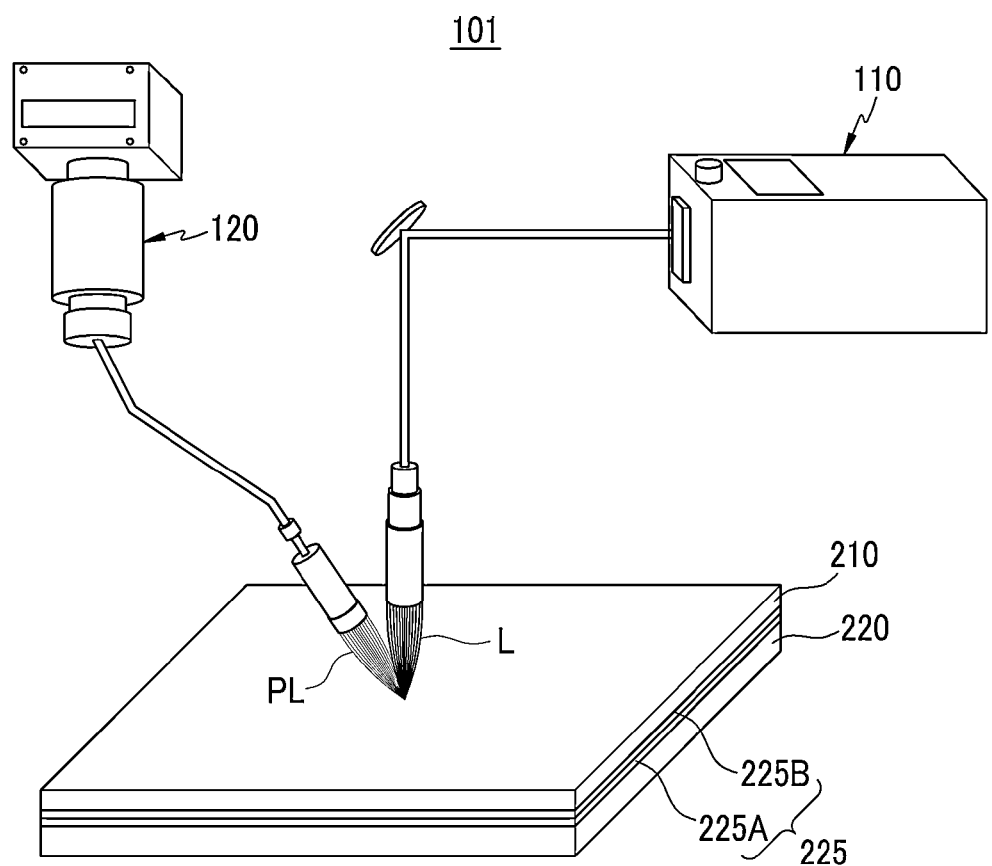
FIG. 1 shows a schematic diagram of a device used for inspecting a polysilicon layer, according to an exemplary embodiment.

The invention is described more fully hereinafter with reference to the accompanying drawings, in which exemplary embodiments of the invention are shown. As those skilled in the art would realize, the described embodiments may be modified in various different ways, all without departing from the spirit or scope of the present invention.

In addition, parts not related to the description are omitted for clear description of the exemplary embodiment, and like reference numerals designate like elements and similar constituent elements throughout the specification.

In the drawings, the sizes and thicknesses of the components are merely shown for convenience of explanation, and therefore the present invention is not necessarily limited to the illustrations described and shown herein.

In the drawings, the thickness of layers, films, panels, regions, etc., are exaggerated for clarity. It will be understood that when an element such as a layer, film, region, or substrate is referred to as being "on" another element, it can be directly on the other element or intervening elements may also be present.

FIG. 1 shows a schematic diagram of a device used for a method for inspecting a polysilicon layer, according to an exemplary embodiment. As shown in FIG. 1, a polysilicon layer inspecting device 101 includes a light source 110 and a detector 120.

A polysilicon layer 210, which is an inspection target used in a method for inspecting a polysilicon layer, according to an exemplary embodiment, is formed on a substrate 220, and is crystallized by, for example, a solid phase crystallization method, an excimer laser annealing (ELA) crystallization method, or a super grain silicon (SGS) crystallization method. The substrate 220 can be formed with a dielectric material, and can be a glass substrate on which an insulation layer 225 is formed. The insulation layer 225 can include a silicon oxide ($SiO_2$) layer 225A, a silicon nitride ($SiN_x$) layer 225B, or a bilayer thereof. The insulation layer 225 prevents impurities from being diffused into the polysilicon layer 210 from the substrate 220. The polysilicon layer 210 can be 1 to 300 nm thick, and in detail, it can be 30 to 100 nm thick.

The light source 110 outputs excitation light (L) to a surface of the polysilicon layer 210. The detector 120 detects a photoluminescence signal (PL) generated by the polysilicon layer 210. The photoluminescence signal (PL) detected by the detector 120 is transmitted to a controller (not shown), and the layer quality of the polysilicon layer 210 is estimated by determining the intensity and spectrum of the photoluminescence signal (PL), using the controller.

When the polysilicon layer 210 is less than 300 nm thick, a surface area to thickness ratio is relatively high, such that a surface recombination velocity of free carriers generated by the excitation light (L) is relatively fast, and the life-span of the free carriers becomes is relatively short, thereby causing a substantial reduction in the intensity of the photoluminescence signal (L). Further, when the polysilicon layer 210 is inspected by using visible or infrared rays that are generally used for photoluminescence study of silicon, a majority of the excitation light (L) passes through the polysilicon layer 210 and into the substrate 220. As a result, light absorption in the visible and infrared spectrum is relatively low. Because of this, the photoluminescence signal (PL) generated by the substrate 220 becomes greater than the signal generated by the polysilicon layer 210. Thus, it may be difficult to distinguish between the signals.

However, according to an exemplary embodiment a method is provided where the photoluminescence signal (PL) can be generated by the thin-film polysilicon layer 210 formed on the substrate 220 made of a dielectric material. In particular, the method includes using a pulsed UV laser beam as the excitation light (L) radiated onto the polysilicon layer 210. The pulsed beam has an average power of 1 to 10 W/cm$^2$, a peak power of 100 to 1000 W/cm$^2$, and an optical wavelength range of 300 to 400 nm.

To increase the efficiency of the photoluminescence signal (PL) to a detectable level, the free carriers generated by the excitation light (L) should not be allowed to rapidly die out, and since the ratio of surface area versus thickness of the polysilicon layer 210 is relatively high, the surface recombination velocity of the free carriers generated by the excitation light (L) is relatively fast, and the free carriers may rapidly die out due to the recombination. Therefore, to increase the efficiency of the photoluminescence signal (PL), the recombination may be blocked and a carrier trap, which is a key point of the recombination, should be saturated. To saturate the carrier trap, the excitation light (L) should have a power of at least 170 W/cm$^2$. The thermal conductivity of the substrate 220 is generally lower than that of the polysilicon layer 210. As such, if a high power excitation light is radiated onto the polysilicon layer 210, the polysilicon layer 210 may be thermally damaged or overheated, thereby failing to provide a uniform measurement.

To solve this and or other problems, the photoluminescence signal (PL) used in the present method may be generated by using the excitation light (L) having the average power of 1 to 10 W/cm$^2$ and the peak power of 100 to 1000 W/cm$^2$. When the average power is greater than 10 W/cm$^2$, the substrate may be heated, so that the polysilicon layer 210 may be damaged.

The peak power should be greater than 100 W/cm$^2$, so as to saturate the carrier trap on the thin-film surface. The peak power should be less than 1000 W/cm$^2$, so as to prevent the polysilicon layer 210 from being damaged. For example, the peak power should range from 300 to 500 W/cm$^2$.

The pulsed UV laser beam used as the excitation light (L) can have a wavelength with a range of 300 to 400 nm. That is, in order to generate the free carriers, a sample should be irradiated with light that has a photon energy that is greater than a semiconductor band gap of the polysilicon layer 210. Concurrently, the light should be efficiently absorbed into the thin-film polysilicon layer 210. The band gap of silicon is 1.12 eV (which is a value that corresponds to infrared light), and light is efficiently absorbed into a thin film that is less than 300 nm thick, when the photon energy is greater than 3 eV (which is a value that corresponds to ultraviolet (UV) light). Therefore, when the light within the range of 300 to 400 nm is used, free carriers are generated, the rate of absorption into the thin-film polysilicon layer 210 is increased, and most of the light is absorbed by the polysilicon layer 210. That is, most of the excitation light (L) is absorbed by the polysilicon layer 210 and fails to reach the substrate 220, thereby minimizing the photoluminescence signal (PL) generated by the substrate 220.

According to an exemplary embodiment, the photoluminescence signal (PL) is acquired with a sufficiently high efficiency, without causing any thermal damage to the thin-film polysilicon layer 210.

A test for measuring a photoluminescence signal (PL) from a polysilicon layer by using the method for inspecting a polysilicon layer, according to an Example 1 and a Comparative Example, will now be described.

In Example 1, an SiN$_x$ layer that is 300 nm thick and a SiO$_2$ layer that is 150 nm thick are stacked on a substrate 220 that is 0.7 mm thick, to form an insulation layer 225. A polysilicon layer 210 having grains of 300 to 600 nm and that is 45 nm thick is formed thereon by excimer laser annealing (ELA) crystallization. Excitation light (L) having a wavelength of 355 nm, a pulse duration time of 15 ns, an iteration rate of 200 kHz, and an average beam power of 10 mW, and that is focused with a spot of 1 mm (i.e., average power of 1 W/cm$^2$), is radiated onto the surface of the polysilicon layer 210. Here, the peak power of the excitation light (L) is 333 W/cm$^2$.

A photoluminescence signal (PL) generated by the excitation light (L) is received by a detector 120. An objective lens with an image space numerical aperture (NA) of 0.33 and magnification of 1:15 is used as the detector 120, and an InGaAs light detecting array (i.e., a Xeva-1.7-320 infrared ray camera) cooled to −70° C. integrates a signal for one second. In this way, a well-defined photoluminescence signal (PL) was acquired.

In Comparative Example 1, an SiN$_x$ layer that is 300 nm thick and a SiO$_2$ layer that is 150 nm thick are stacked on a substrate 220 that is 0.7 mm thick, to form an insulation layer 225. A polysilicon layer 210 that has grains of 300 to 600 nm and is 45 nm thick is formed thereon by excimer laser annealing (ELA) crystallization. Excitation light (L) having a wavelength of 355 nm, a pulse duration time of 15 ns, an iteration rate of 200 kHz, and an average power of 10 mW, and that is focused with a spot of 1 mm, is radiated onto the surface of the polysilicon layer 210. Here, the average power of the excitation light (L) corresponds to 1 W/cm$^2$.

A photoluminescence signal (PL) generated by the excitation light (L) is received by a detector 120. An objective lens with an image space numerical aperture (NA) of 0.33 and a magnification of 1:15 is used as the detector 120. An InGaAs light detecting array (i.e., a Xeva-1.7-320 infrared ray camera) cooled at −70° C. is used to integrate a signal for one second. In Comparative Example 1, the photoluminescence signal (PL) is not detected.

That is, regarding excitation of the thin-film polysilicon layer 210 that is 45 nm thick and is formed under the same condition, as in the case of Embodiment 1, the excitation light (L) with low energy having the average power of 1 W/cm$^2$, the peak power is set to be 100 to 1000 W/cm$^2$, and the well-defined photoluminescence signal (PL) is accordingly acquired, and in the case of Comparative Example 1, the excitation light (L) having the average power of 1 W/cm$^2$ is used, its power is insufficient, and the photoluminescence signal (PL) cannot be observed.

Figure 2:
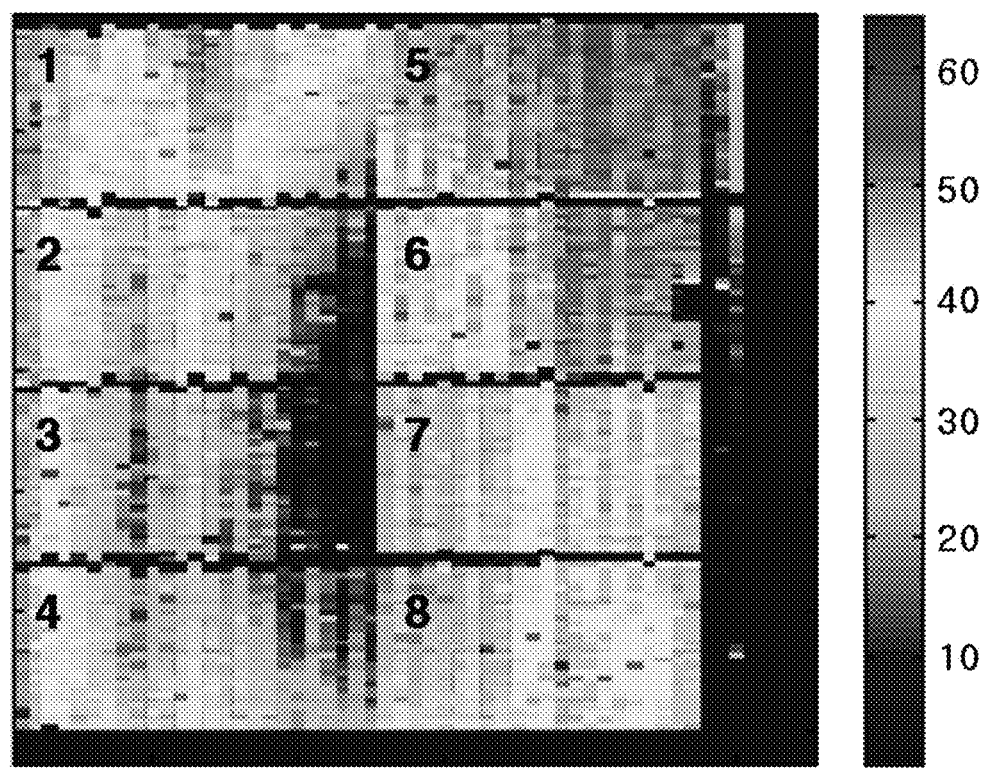
FIG. 2 shows an image acquired by photographing a result of detecting a photoluminescence signal (PL) acquired from an exemplary embodiment.

FIG. 2 shows an image acquired by photographing a result of detecting a photoluminescence signal (PL) acquired from Example 1. As shown in FIG. 2, the test panel is divided into eight areas (areas 1 to 8) and the test panel is thermally treated with eight different levels of laser power, so that the polysilicon layer 210 may have different crystallization degrees in the respective areas. For the acquired test panel, excitation light (L) formed with a wavelength of 355 nm, a pulse duration time of 15 ns, an iteration rate of 200 kHz, and an average power of 1 W/cm$^2$, and that is focused with a spot of 10 mm, is radiated to the surface of the polysilicon layer 210. Here, peak power of the excitation light (L) is 333 W/cm$^2$.

The acquired photoluminescence signal (PL) is detected in a like manner of Exemplary Embodiment 1. The photoluminescence signal (PL) generated by the inspecting method according to the present exemplary embodiment is sufficiently strong, so a high-quality image is acquired as shown in FIG. 2. In FIG. 2, the right top area (area 5) represents a part that is thermally treated with the highest level of laser power, and the left bottom area (area 4) indicates a part that is thermally treated with the lowest level of laser power. Further, a center part of the test panel is insufficiently crystallized as compared to other parts, since a thickness of the sample of the polysilicon layer 210 is non-uniform. As shown in FIG. 2, a difference of the crystallization degrees is clearly determined from the photoluminescence signal (PL) generated by the inspecting method, according to the present exemplary embodiment.

Figure 3:
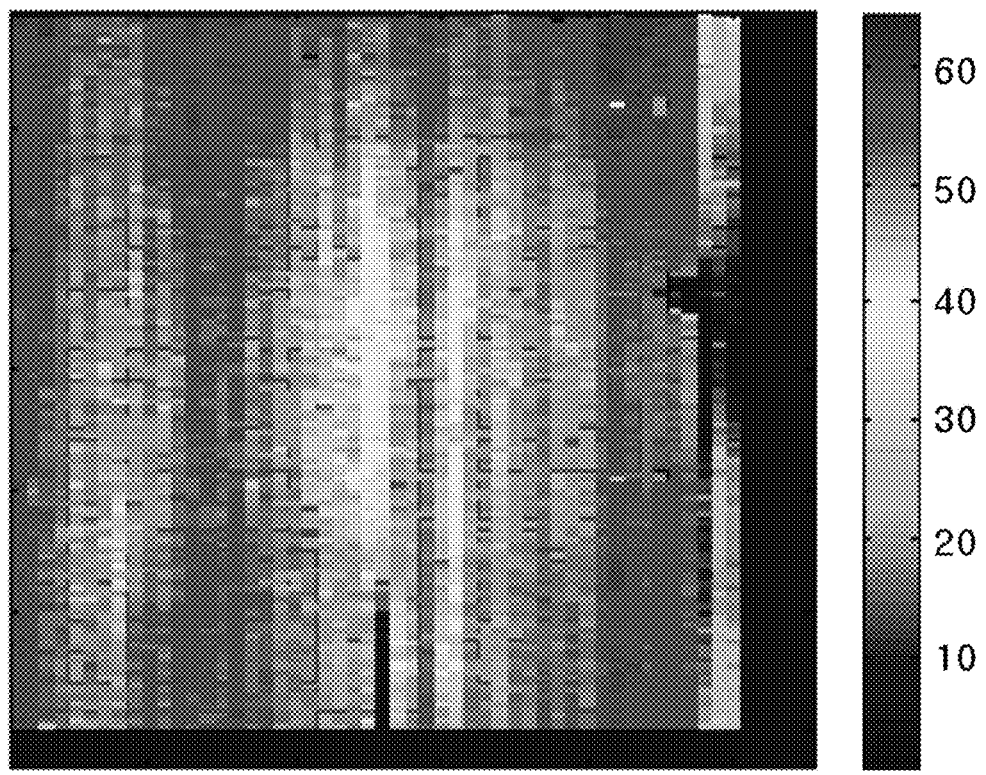
FIG. 3 shows an image acquired by photographing a result of detecting a photoluminescence signal (PL) acquired from an exemplary embodiment.

FIG. 3 shows an image acquired by photographing a result of detecting a photoluminescence signal (PL) acquired from Example 2. In Example 2, an SiN$_x$ layer that is 300 nm thick and a SiO$_2$ layer that is 150 nm thick are stacked on a substrate 220 that is 0.7 mm thick, to form an insulation layer. A polysilicon layer 210 that has grains of 300 to 600 nm and is 45 nm thick is formed thereon by excimer laser annealing (ELA) crystallization. In this instance, crystallization is performed so that the test panel may be uniformly thermally treated with laser power provided to a general process. For the acquired test panel, excitation light (L) formed with a wavelength of 355 nm, a pulse duration time of 15 ns, an iteration rate of 200 kHz, and an average power of 1 W/cm$^2$, and that is focused with a spot of 10 mm, is radiated to the surface of the polysilicon layer 210, and is then detected. Here, peak power of the excitation light (L) was 333 W/cm$^2$.

The acquired photoluminescence signal (PL) is detected in a like manner of Embodiment 1. The photoluminescence signal (PL) generated by the inspecting method according to the present exemplary embodiment is sufficiently strong, so a high-quality image is acquired as shown in FIG. 3. It is determined from FIG. 3 that the thickness of the sample of the polysilicon layer 210 is non-uniform and most areas, except for the center part that is insufficiently crystallized as compared to other parts, are appropriately crystallized. That is, defects are clearly determined from the photoluminescence signal (PL) generated by the inspecting method, according to the present exemplary embodiment.

It is determined through the above-described exemplary embodiment, comparative examples, and application examples that the defect state of the polysilicon layer can be inspected with high efficiency without damaging the polysilicon layer when the method for inspecting the polysilicon layer according to the exemplary embodiment is used.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. A method for inspecting a polysilicon layer, comprising:
   radiating excitation light onto the polysilicon layer; and
   detecting a photoluminescence signal generated in the polysilicon layer by the excitation light,
   wherein:
   the excitation light has an average power in a range of 1 W/cm$^2$ to 10 W/cm$^2$;
   a peak power of the excitation light is in a range of 300 W/cm$^2$ to 500 W/cm$^2$; and
   the polysilicon layer has a thickness in a range of 1 nm to 300 nm.

2. The method of claim 1, wherein the excitation light has a wavelength in a range of 300 nm to 400 nm.

3. The method of claim 1, wherein the polysilicon layer is disposed on a substrate comprising a dielectric material.

4. The method of claim 3, wherein an insulation layer is disposed between the polysilicon layer and the substrate.

5. The method of claim 4, wherein the insulation layer comprises a silicon oxide (SiO$_2$) layer, a silicon nitride (SiN$_x$) layer, or both a silicon oxide (SiO$_2$) layer and a silicon nitride (SiN$_x$) layer.

6. The method of claim 3, wherein the substrate comprises glass.

7. A method for inspecting a polysilicon layer, comprising:
   radiating a pulsed laser beam onto the polysilicon layer; and
   detecting a photoluminescence signal generated in the polysilicon layer by the laser beam,
   wherein:
   the laser beam has:
     an average power of from 1 W/cm$^2$ to 10 W/cm$^2$;
     a peak power in a range of 300 W/cm$^2$ to 500 W/cm$^2$;
     a pulse duration time of 15 ns;
     an iteration rate of 200 kHz; and
     a wavelength in a range of 300 nm to 400 nm; and
   the thickness of the polysilicon layer is in a range of 1 nm to 300 nm.

8. The method of claim 7, wherein:
   the polysilicon layer is disposed on an insulating layer that is about 0.7 mm thick; and
   the insulating layer is disposed on a dielectric substrate.

9. The method of claim 1, wherein the polysilicon layer is not damaged from radiated excitation light.

10. The method of claim 7, wherein the polysilicon layer is not damaged from radiated excitation light.

* * * * *